US006254577B1

(12) United States Patent
Huet

(10) Patent No.: US 6,254,577 B1
(45) Date of Patent: Jul. 3, 2001

(54) HYPODERMIC NEEDLE PROTECTOR

(75) Inventor: Jean-Max Huet, Clichy (FR)

(73) Assignee: Vygon (FR)

( * ) Notice: Subject to any disclaimer, the term of this patent is extended or adjusted under 35 U.S.C. 154(b) by 0 days.

(21) Appl. No.: 09/328,829

(22) Filed: Jun. 8, 1999

(30) Foreign Application Priority Data

Jun. 11, 1998 (FR) ............................................ 98 07361

(51) Int. Cl.[7] ............................................ A61M 5/00

(52) U.S. Cl. ............................................ 604/263; 604/192

(58) Field of Search ............................................ 604/192, 263, 604/187, 198, 177

(56) References Cited

U.S. PATENT DOCUMENTS

| | | | | |
|---|---|---|---|---|
| 4,950,249 | | 8/1990 | Jagger et al. | 604/192 |
| 4,982,842 | * | 1/1991 | Hollister . | |
| 5,078,693 | * | 1/1992 | Shine . | |
| 5,135,509 | * | 8/1992 | Olliffe | 604/192 |
| 5,242,417 | * | 9/1993 | Paudler | 604/192 |
| 5,385,556 | * | 1/1995 | Wang et al. . | |
| 5,472,433 | * | 12/1995 | Suzuki | 604/263 |
| 5,490,841 | * | 2/1996 | Landis . | |
| 5,702,369 | | 12/1997 | Mercereau | 604/192 |
| 5,733,265 | * | 3/1998 | Bachman et al. | 604/263 |
| 5,836,920 | * | 11/1998 | Robertson | 604/192 |
| 5,868,716 | * | 2/1999 | Sweeney et al. | 604/263 |
| 5,876,381 | * | 3/1999 | Pond et al. | 604/192 |
| 5,885,249 | * | 3/1999 | Irisawa | 604/111 |
| 5,891,103 | * | 4/1999 | Burns | 604/192 |
| 5,913,846 | * | 6/1999 | Szabo | 604/263 |
| 6,173,868 | * | 1/2001 | DeJonge . | |

FOREIGN PATENT DOCUMENTS

| | | |
|---|---|---|
| 0 589 506 A3 | 3/1994 | (EP) . |
| WO 90/01348 | 2/1990 | (WO) . |
| WO 94/11050 | 5/1994 | (WO) . |

* cited by examiner

*Primary Examiner*—Anhtuan T. Nguyen
*Assistant Examiner*—Jeremy Thissell
(74) *Attorney, Agent, or Firm*—Mason, Kolehmainen, Rathburn & Wyss

(57) ABSTRACT

A hypodermic needle protector constituted by a single piece of molded synthetic resin, said piece having a distal portion which forms a cap in which the distal end portion of the needle is housed, and a proximal portion forming a base in which the proximal end portion of the needle is engaged, said two portions being hinged to each other via a thin zone constituting an elastic effect fold line such that manual action makes it possible to tilt the cap so as to reveal the needle and such that the cap returns on its own to its protective position after said manual action ceases, wherein the base of the protector is designed so that the cap is caused to tilt by applying manual action to the base.

6 Claims, 5 Drawing Sheets

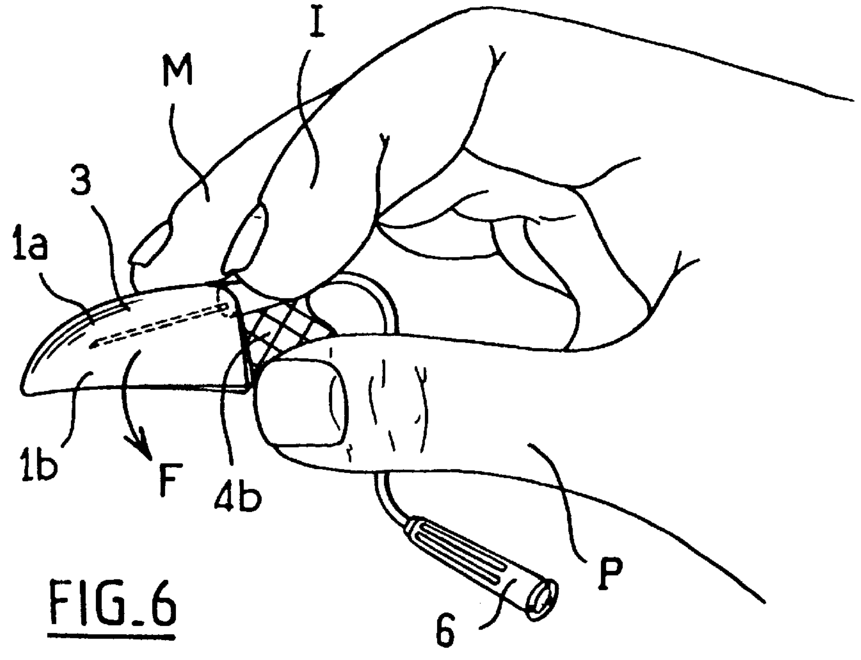
FIG_6
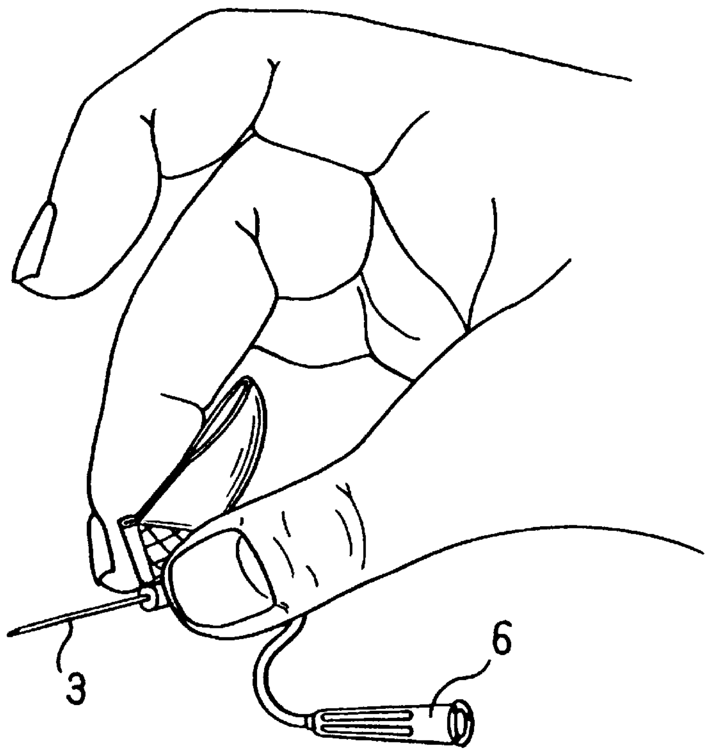
FIG_7

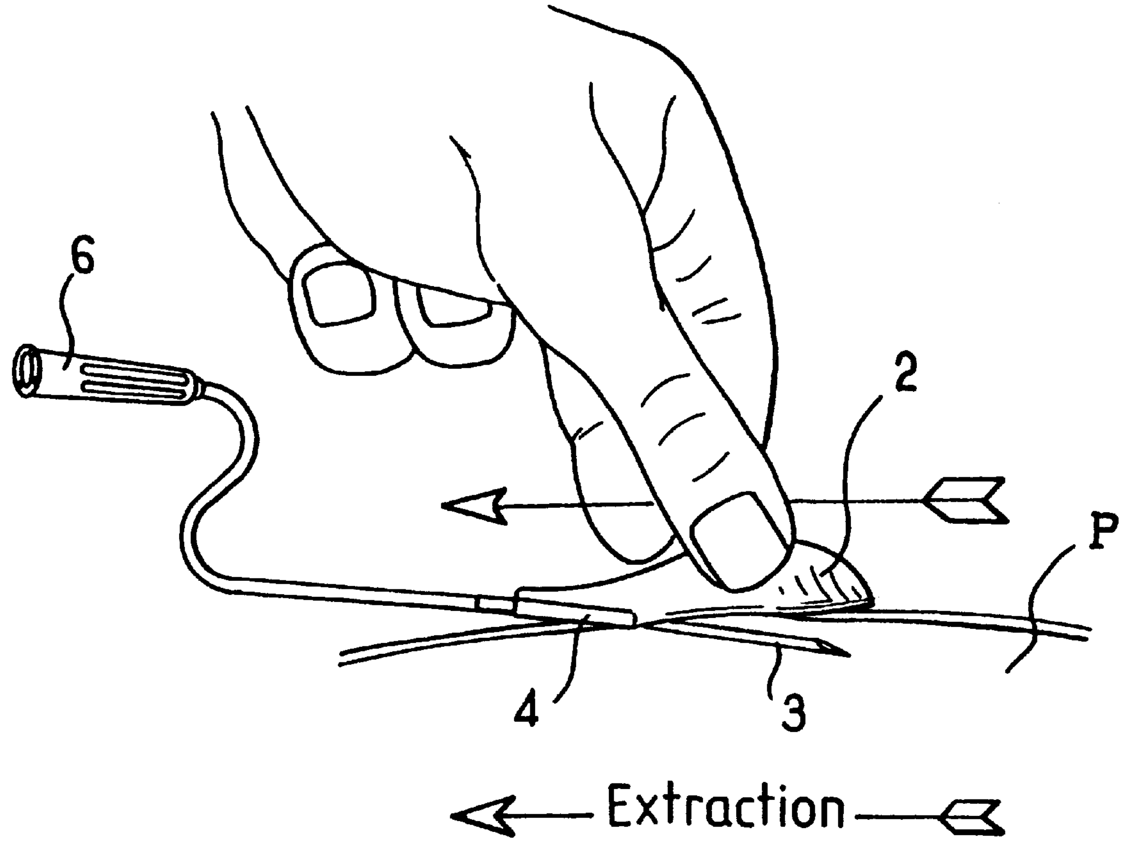
FIG_9

HYPODERMIC NEEDLE PROTECTOR

The present invention relates to a hypodermic needle protector, in particular for an epicardial needle.

BACKGROUND OF THE INVENTION

A needle protector for a hypodermic needle is known that is constituted by a single piece of molded synthetic resin, said piece having a distal portion which forms a cap in which the distal end of the needle is received, and a proximal portion forming a base in which the proximal end of the needle is engaged, said two portions being hinged to each other via a thin zone constituting an elastic effect fold line such that manual action makes it possible to tilt the cap so as to reveal the needle and such that the cap returns on its own to its protective position after said manual action ceases, as described in the publication U.S. Pat. No. 5,693,022.

Compared with prior devices requiring return springs, that type of protector has the advantage of the cap returning on its own to its protective position after the manual action which moves it away has ceased.

This provides good security at low cost against accidental pricking.

In the embodiments described in the above-mentioned publication, the protector has a grip finger on its cap-forming portion, on which the user must act in order to tilt the cap.

The user must therefore both hold the base of the protector so as to manipulate the needle, while simultaneously acting on the finger of the cap so as to reveal the needle.

OBJECT AND SUMMARY OF THE INVENTION

An object of the present invention is to provide a protector that is easier to handle.

According to the invention, this is achieved by designing the base of the protector in such a manner that the cap is tilted by manual action exerted on said base.

In a preferred embodiment, the base has two flaps for grasping that are suitable for being pivoted manually in one direction to cause the cap to tilt.

The operator thus simultaneously holds the needle in the hand and tilts the cap.

BRIEF DESCRIPTION OF THE DRAWINGS

A preferred embodiment of the protector of the invention is described below with reference to the figures of the accompanying drawings, with other characteristics of the present invention appearing from the description and the figures.

In the figures:

FIGS. 6 and 7 are other perspective views showing how an operator can take hold of the protector and manipulate it using the fingers of one hand only;

FIG. 9 is a perspective view showing the initial stage of the operation for extracting the needle.

MORE DETAILED DESCRIPTION

Figure 4:
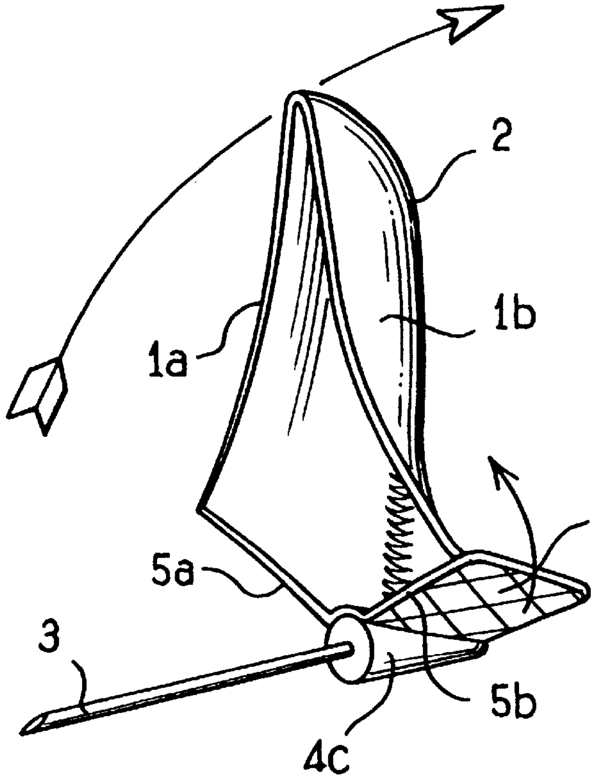
FIGS. 4 and 5 are perspective views of the protector during two successive stages in the operation of disengaging the needle.
Figure 5:
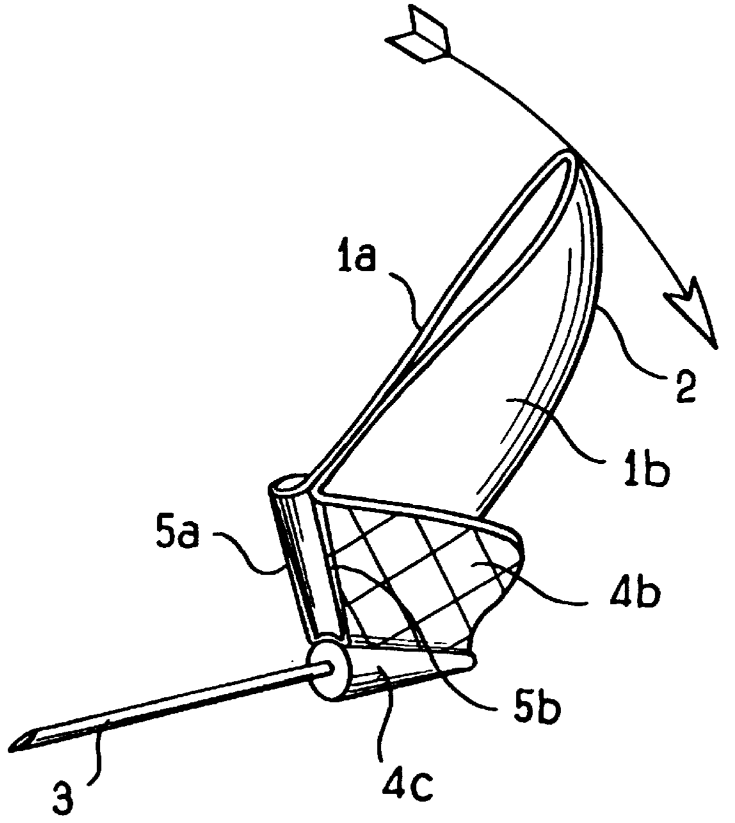

The protector shown in the figures comprises a cap (1) constituted by two walls (1*a*; 1*b*) meeting obliquely along a zone (2) which runs along the needle (3) and which rises ahead of the tip (3*a*) of the needle, so as to give the cap a V-shaped cross-section as can be seen in the figures and in particular in FIG. 4, which section flares at an angle that decreases as the plane of the section comes closer to the end of the cap.

According to the invention, the protector also has a base (4) constituted by two flaps (4*a*; 4*b*) hinged laterally to a central hub (4*c*) in which the proximal end portion of the needle (3*b*) is engaged, the two flaps respectively extending the two walls (1*a*; 1*b*) of the cap to which they are connected via thin zones (5*a*; 5*b*).

The flaps are hinged to the hub by two hinges (5*c*; 5*d*) constituted by thin-wall portions.

Figure 1:
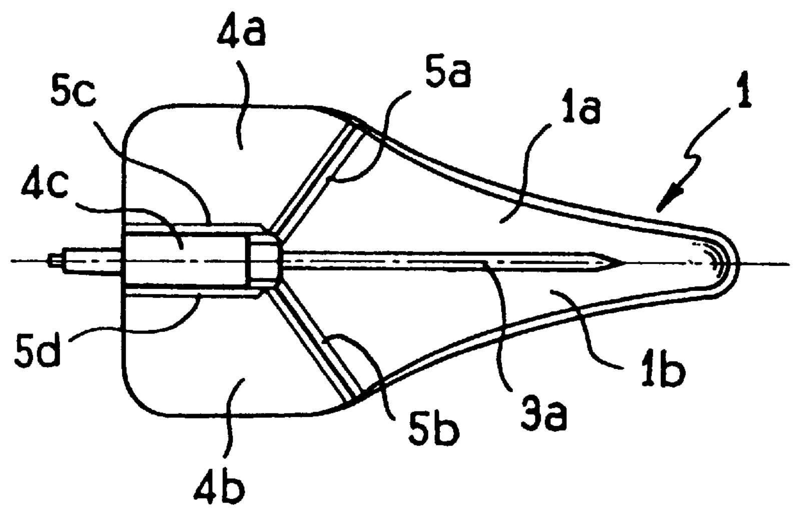
FIG. 1 is a plan view of the protector in its needle-protecting configuration.
Figure 2:
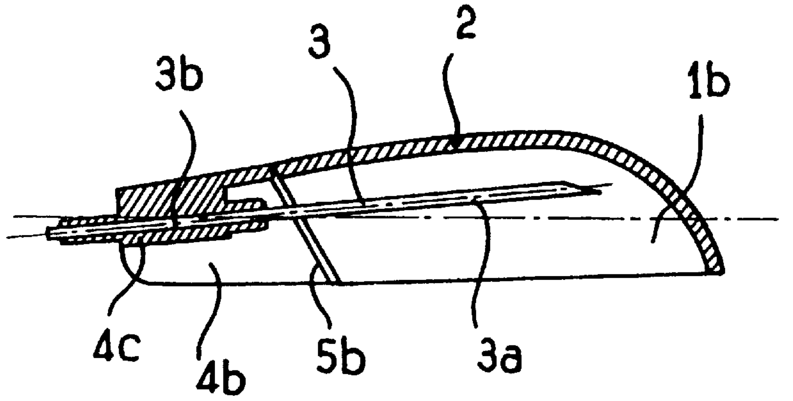
FIG. 2 is a section through the FIG. 1 protector on a plane containing the needle.
Figure 3:
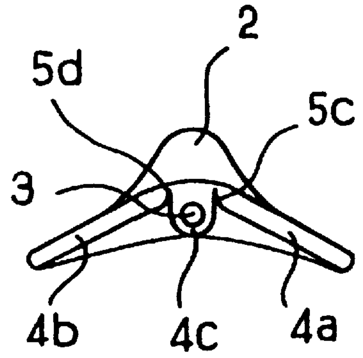
FIG. 3 is a section through the protector on a plane perpendicular to the needle, through the base region thereof.

The major portion of the hub (4*c*) preferably projects from the flaps (4*a*; 4*b*) as can be seen in particular in FIG. 3.

The walls of the cap and the flaps preferably have relatively flexible thin walls so as to avoid being damaged.

The proximal end of the needle preferably passes through the hub so as to be connected to a connector (6).

The wall thickness of the flaps is preferably greater than the wall thickness of the cap.

Finally, it will be observed that in the embodiment shown, the thin zones (5*a*; 5*b*) co-operate with the hub (4*c*) to form a Y-shape.

In operation, the protector is handled while the needle is in position beneath the cap, with the chamfer of the needle tip being visible.

Figure 8:
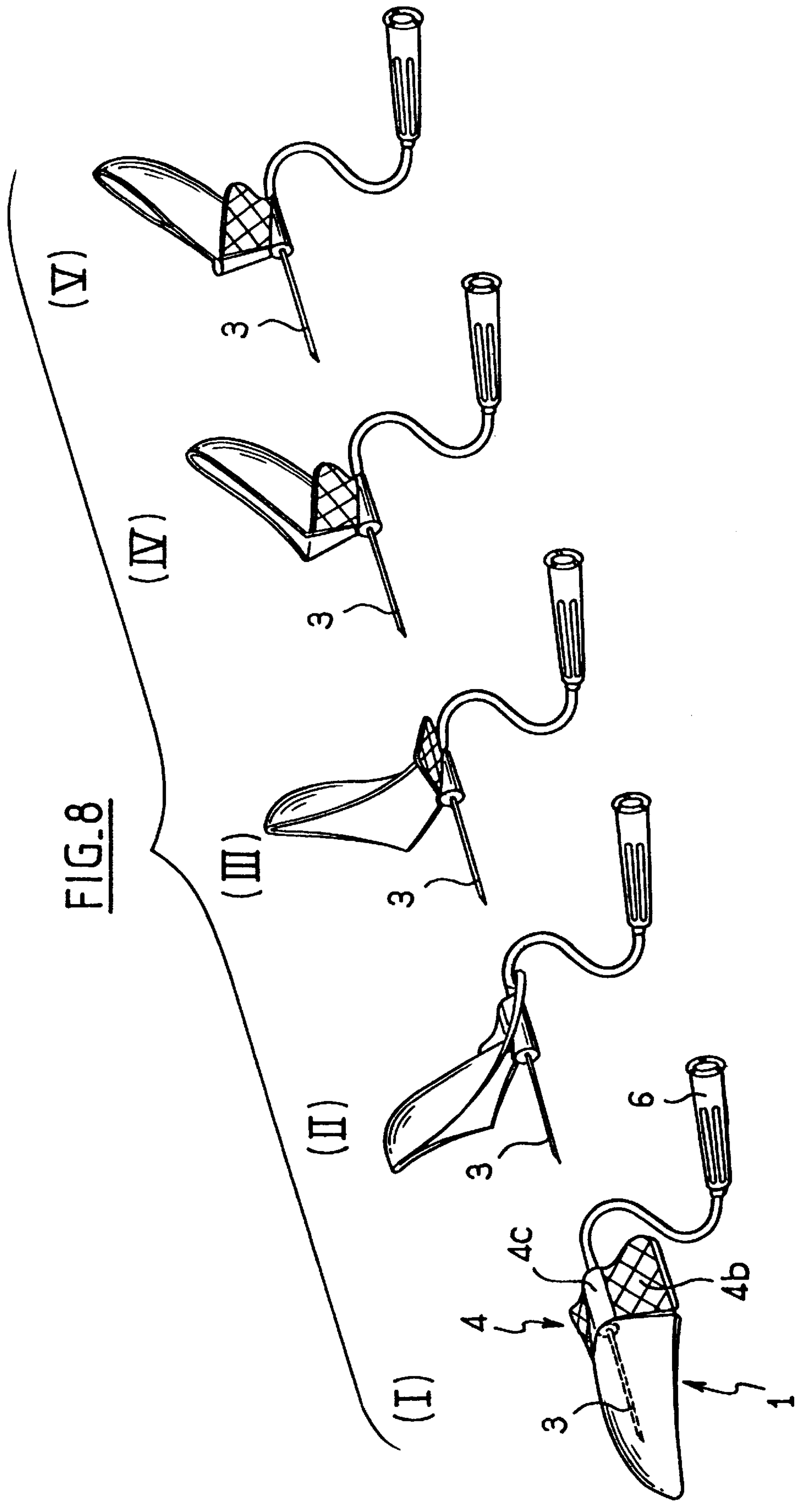
FIG. 8 is a perspective view showing five successive stages in an operation of uncovering the needle for use.

The operator holds the flaps respectively with the thumb (P) and the middle finger (M) while exerting pressure with the index Finger (I) on the hub so as to push them towards the back of the cap as can be seen in FIG. 4, thereby raising the flaps, thus causing the cap to tilt upwards and then backwards in the direction of arrow (F), progressively releasing the needle (3) which is to be found beneath the cap, as can be seen in FIG. 8.

It will be observed that in the position where the needle is uncovered, ready for use, the operator is holding the device essentially between the thumb and the middle finger, which are pressing the two flaps of the base against each other.

After the puncture has been made, if the needle is to be left in place, the two flaps allow it to be fixed to the patient by means of adhesive tape, in conventional manner.

To extract the needle, it is not necessary to fold back the flaps which are then flat against the skin (P), all that is required is for the device to be taken hold of by the cap (FIG. 9) and the needle comes back automatically into the cap as soon as it has been extracted from the skin.

The invention is not limited to the embodiment described above.

What is claimed is:

1. A hypodermic needle protector for a needle extending from a proximal needle end portion to a distal needle end portion, said protector comprising:

a single protector piece of molded synthetic resin having a distal protector portion and a proximal protector portion, said single protector piece pivotable between a first covering position and a second uncovering position;

said distal protector portion forming a cap housing said distal needle end portion when said single protector piece is in said first position and having two walls meeting obliquely along a zone which extends along said needle and which rises ahead of said distal needle end portion such that said cap has a generally V-shaped cross-section formed by said two walls with an opening angle thereof decreasing as said walls of said cap approach a distal end of said cap; and said proximal protector portion having a hub in which said proximal needle end portion is affixed, said proximal protector portion further comprising two flaps hinged laterally to said hub by respective hinges with each of said two flaps respectively extending from one of said two walls of said cap and is hinged to one of said two walls by a thin connecting zone forming an elastic effect fold line such that upon said flaps being pivoted on said hub toward each other, said cap pivots from said first covering position to said second uncovering position and upon a release of said flaps, said flaps pivot away from each other and said cap returns to said first covering position.

2. A method of positioning a hypodermic needle protector relative to a hypodermic needle, said protector including a single protector piece of molded synthetic resin having a distal protector portion, having a proximal protector portion, and pivotable between a first covering position and a second uncovering position relative to said needle which extends from a proximal needle end portion to a distal needle end portion, said method comprising:

affixing a hub of said proximal protector portion with respect to said proximal needle end portion such that said distal protector portion forms a cap housing said distal needle end portion when said single protector piece is in said first position and having two walls meeting obliquely along a zone which extends along said needle and which rises ahead of said distal needle end portion such that said cap has a generally V-shaped cross-section formed by said two walls with an opening angle thereof decreasing as said walls of said cap approach a distal end of said cap;

compressing two flaps hinged laterally to said hub by respective hinges, each of said flaps respectively extending from one of said two walls of said cap and is hinged to one of said two walls by a thin connecting zone forming an elastic effect fold line such that when said flaps are pivoted on said hub toward each other, said cap pivots from said first covering position to said second uncovering position; and releasing said flaps such that said flaps pivot away from each other causing said cap to return to said first covering position.

3. A protector according to claim 1, in which said two flaps and said two walls are flexible.

4. A protector according to claim 3, in which said two walls are thinner than said two flaps.

5. A protector according to claim 1, in which the hub has the proximal needle end portion passing therethrough.

6. A protector according to claim 5, in which said thin connecting zones connecting said flaps and said walls form a Y-shape with the hub.

* * * * *